US010791985B2

United States Patent
Olivier

(10) Patent No.: US 10,791,985 B2
(45) Date of Patent: Oct. 6, 2020

(54) CARDIO-KINETIC CROSS-SPECTRAL DENSITY FOR ASSESSMENT OF SLEEP PHYSIOLOGY

(71) Applicant: LifeQ Global Limited, Dublin (IE)

(72) Inventor: Laurence Richard Olivier, Alpharetta, GA (US)

(73) Assignee: LifeQ Global Limited, Dublin (IE)

( * ) Notice: Subject to any disclaimer, the term of this patent is extended or adjusted under 35 U.S.C. 154(b) by 605 days.

(21) Appl. No.: 15/393,398

(22) Filed: Dec. 29, 2016

(65) Prior Publication Data
US 2017/0181691 A1 Jun. 29, 2017

Related U.S. Application Data

(60) Provisional application No. 62/272,223, filed on Dec. 29, 2015.

(51) Int. Cl.
*A61B 5/00* (2006.01)
*A61B 5/11* (2006.01)
(Continued)

(52) U.S. Cl.
CPC .......... *A61B 5/4812* (2013.01); *A61B 5/0006* (2013.01); *A61B 5/0205* (2013.01);
(Continued)

(58) Field of Classification Search
CPC ... A61B 5/4812; A61B 5/0006; A61B 5/0205; A61B 5/0402; A61B 5/1102;
(Continued)

(56) References Cited

U.S. PATENT DOCUMENTS

2004/0193068 A1* 9/2004 Burton ................. A61B 5/0476
600/544
2005/0256418 A1 11/2005 Mietus
(Continued)

FOREIGN PATENT DOCUMENTS

EP 16722798 A1 * 4/2016 ............ A61B 5/05
EP 16722798.2 A * 2/2018 ............ G01S 13/56
(Continued)

OTHER PUBLICATIONS

U.S. Appl. No. 62/207,687, filed Aug. 2015, Shouldice et al.*
(Continued)

*Primary Examiner* — Erin M Piateski
(74) *Attorney, Agent, or Firm* — Smith Gambrell & Russell LLP

(57) ABSTRACT

The invention comprises methods and systems capable of processing simultaneously measured cardiac and motion signals, selecting from said signals the optimal cardiac and motion signal combination for cross spectral density calculations and, hereafter, itemizing the shared information in terms of the individual constituent frequencies and the effect exerted upon said frequencies by common underlying physiological states. The information is passed through a classifier, where said information is used to quantify the underlying physiological states, exemplified by but not limited to, sleep stage, quality and/or disorders that affect sleep stability. Inferences made by the methods described, for example, can be employed to aid home based sleep analysis and automated screening of patients with sleep disorders.

20 Claims, 3 Drawing Sheets

(51) Int. Cl.
*A61B 5/0205* (2006.01)
*A61B 5/0402* (2006.01)
*A61B 5/024* (2006.01)

(52) U.S. Cl.
CPC .......... *A61B 5/0402* (2013.01); *A61B 5/1102* (2013.01); *A61B 5/4815* (2013.01); *A61B 5/6802* (2013.01); *A61B 5/7221* (2013.01); *A61B 5/7278* (2013.01); *A61B 5/742* (2013.01); *A61B 5/02416* (2013.01); *A61B 2562/0219* (2013.01)

(58) Field of Classification Search
CPC ... A61B 5/4815; A61B 5/6802; A61B 5/7221; A61B 5/7278; A61B 5/742; A61B 5/02416; A61B 2562/0219
USPC .......................................................... 600/31
See application file for complete search history.

(56) References Cited

U.S. PATENT DOCUMENTS

| | | |
|---|---|---|
| 2006/0041201 A1 | 2/2006 | Behbehani |
| 2007/0032733 A1* | 2/2007 | Burton ............... A61B 5/02405 600/509 |
| 2010/0217099 A1 | 8/2010 | Leboeuf et al. |
| 2010/0240982 A1 | 9/2010 | Westbrook et al. |
| 2012/0203077 A1* | 8/2012 | He ..................... A61B 5/02055 600/301 |
| 2014/0206946 A1 | 7/2014 | Kim et al. |
| 2015/0164409 A1* | 6/2015 | Benson ................. G16H 50/30 600/301 |
| 2015/0190086 A1* | 7/2015 | Chan ..................... A61B 5/4812 600/301 |
| 2015/0230750 A1 | 8/2015 | McDarby et al. |
| 2016/0361021 A1 | 12/2016 | Salehizadeh et al. |

FOREIGN PATENT DOCUMENTS

| | | |
|---|---|---|
| WO | 2006048852 | 5/2006 |
| WO | 2012025622 | 3/2012 |
| WO | 2015103558 | 7/2015 |

OTHER PUBLICATIONS

International Search Report and Written Opinion issued by the International Search Authority dated Mar. 29, 2017; 5 pages.

Extended European Search Report issued by the European Search Report dated Jul. 9, 2019; 9 pages.

Christensen, Julie A., et al., "Sleep-Stage Transitions During Polysomnographic Recordings as Diagnostic Features of Type 1 Narcolepsy", Sleep Medicine Journal, vol. 16, No. 12, Jul. 7, 2015; 9 pages.

* cited by examiner

CARDIO-KINETIC CROSS-SPECTRAL DENSITY FOR ASSESSMENT OF SLEEP PHYSIOLOGY

CLAIM OF PRIORITY

The present application claims priority from Provisional Patent Application No. 62/272,223, filed on Dec. 29, 2015, the disclosure of which is relied upon and incorporated herein in its entirety by reference.

FIELD

The present invention relates to the field of non-invasive digital health monitoring, physiological signal processing, and computation of biological data. In particular, the present invention is directed to systems and methods to detect, measure, and assess physiological states related to the sleep/wake stages of an individual.

BACKGROUND

Sleep is a natural, periodically recurring state of immobility of humans during which the nervous system is largely inactive, the eyes are closed, postural muscles are relaxed, and consciousness is practically suspended. However, the brain remains active. In contrast, wakefulness is defined as the absence of sleep and is demonstrated by consciousness, awareness, and deliberate activity of an individual. While the primary function of sleep is known to be restoration, the exact purpose of sleep is unknown. Studies examining the effects of sleep deprivation have shown that effective sleep is critical for both physical and mental health. In addition, it is inferred that sleep serves a critical role in memory consolidation as well as neuroplasticity. Experiencing satisfactory quality of sleep is imperative and has been proven to impact on various aspects of waking life, of which mental acuity, productivity, physical vitality, and emotional balance are paramount.

Sleep disorders, also termed somnipathies, are medical disorders of sleep patterns and are exemplified by, but not limited to, sleep epilepsy, obstructive sleep apnea, narcolepsy, idiopathic hypersomnia, cataplexy and night terrors. These disorders impact harshly on a subject's life and can vary from conditions as benign as slight weight gain to something as serious as weakened immune response, depression, and accidental death.

Currently, only one gold standard method for sleep assessment, namely Polysomnography (PSG), exists. PSG entails the recording of brain dynamics, oxygen level in the blood, heart and breathing rate, as well as eye movements and skeletal muscle activation. Even though this method is comprehensive, it is costly and also time consuming, as it necessitates the individual being monitored to spend at least one night in a sleep clinic. In addition, for some subjects, attending a sleep clinic for monitoring is almost impossible. For example, rural areas rarely have sleep clinics or within reasonable distances of such facilities, leaving rural residents with either foregoing the testing or traveling great distances for the monitoring. Moreover, when a subject is able to make it to a sleep clinic for the sleep study, the subject is fitted with numerous surface electrodes and wiring. In such instances, the monitoring devices could cause undue influence on the sleep of the subject, due to discomfort and the requirement for the subject to divert from their accustomed sleeping positions.

Hereby, we recognized that the existing mechanisms used to assess sleep stages are prohibitively expensive, time consuming, and pose unavoidable discomfort to the subject. Therefore, a strong need exists for a mechanism to assess sleep stages in an inexpensive and non-invasive manner which poses minimal or zero discomfort to the subject.

SUMMARY

The claimed invention comprises computer-implemented methods of utilizing a wide range of cardiac and motion signals simultaneously and in a non-invasive manner to assess sleep stages of a subject. In an aspect, the methods can obtain such cardiac and motion signals from a range of data acquisition devices capable of detecting and measuring these signals, databases and cloud-based platforms storing and organizing such information, or any combination thereof. In an aspect, optimal signals for cross—spectral density calculations are selected from said range of cardiac and motion signals, and are shared as itemized information in terms of the individual constituent frequencies and the effect exerted upon said frequencies by common underlying states. Hereafter, the itemized information is passed through a classifier. The classifier can then separate the information into states, as well as make inferences with regards to such sleep states. In an aspect, the states and inferences are exemplified by, but not limited to, sleep stage, sleep quality, sleep stability, and sleep disorders. These inferences can be, for example, employed to aid home based sleep analysis and automated screening of patients with sleep disorders. Moreover, data collected by data acquisition device(s) can also be sent to and relayed between other data acquisition device(s), a mobile device and/or a cloud based platform, through wireless connections and communications. From either the data acquisition device, the mobile device, and/or the cloud based platform, information can be shared with third parties exemplified by, but not limited to medical care, insurance and healthcare providers.

These and other aspects of the invention can be realized from a reading and understanding of the detailed description and drawings.

DETAILED DESCRIPTION AND DRAWING

The following abbreviations are used throughout the detailed description below: ACC—Accelerometer; BCG—Ballistocardiograph; CSD—Cross-spectral density; DSP—Digital signal processing; ECG—Electrocardiogram; HR—Heart rate; PPG—Photoplethysmograph; RR—Interval between successive R—spikes.

In an aspect, the present invention utilizes computer-implemented methods capable of using a wide range of cardiac and motion signals acquired through a non-invasive data acquisition device or made available through either associated cloud-based platforms and databases, or a combination thereof, to monitor and make inferences about an individual's sleep stages (e.g., awake and one of the five sleep stages, 1, 2, 3, 4, and REM, going from 1-REM in order back to stage 1), sleep quality (i.e., sleep quantity and movement within the sleep), sleep stability (i.e., staying asleep), and potential sleep disorders. In an aspect, sleep disorders can be divided into three categories: lack of sleep (e.g., insomnia and sleep deprivation), disturbed sleep (sleep apnea, REM sleep behavior disorder, and restless legs syndrome), and excessive sleep (e.g., narcolepsy, cataplexy, sleep paralysis, and hypnagogic hallucinations).

In an aspect, the present invention utilizes a data acquisition device 101 configured to detect and measure the range of cardiac and motion signals simultaneously, selecting from said range the optimal signals for cross-spectral density calculations, as well as itemize the shared information in terms of the individual constituent frequencies and the effect exerted upon said frequencies by common underlying states. The data acquisition device 101 can include any device that is capable of acquiring data, and more specifically cardiac and motion signals, from a subject. For example, the data acquisition device 101 can include implantable devices (e.g., a chip inserted at a person's wrist), ingestible devices (e.g., a capsule that passes through the digestive system), and nanotechnology systems. In addition, contextual information (i.e. details regarding previously diagnosed conditions and diseases, behavioral habits, diet, and the like that can have impact on the subject's sleeping patterns) can be provided by the subject to the various components (e.g., the data acquisition device, other mobile devices, the cloud-based platform) to be utilized by the systems and methods described herein.

Figure 1:
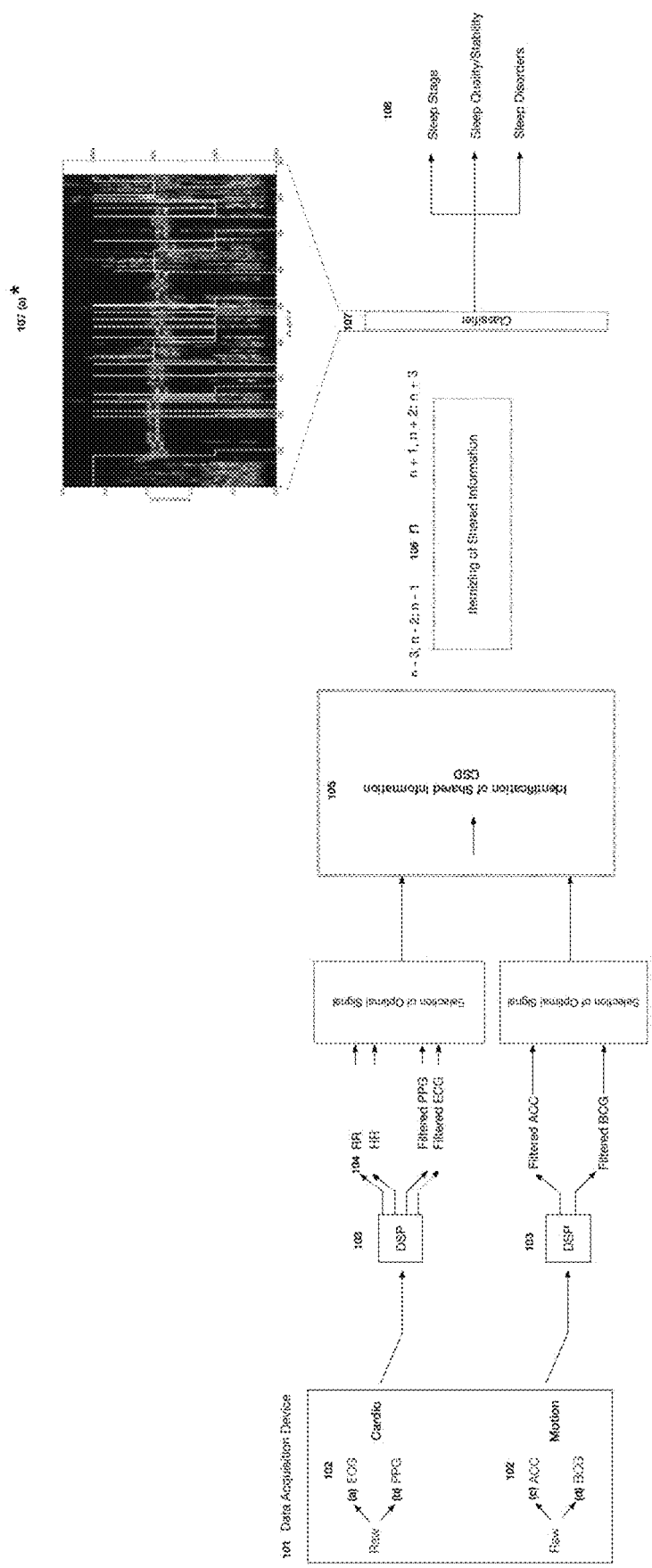
FIG. 1 is a schematic representation of a data acquisition device according to an aspect of the present invention.
Figure 1A:
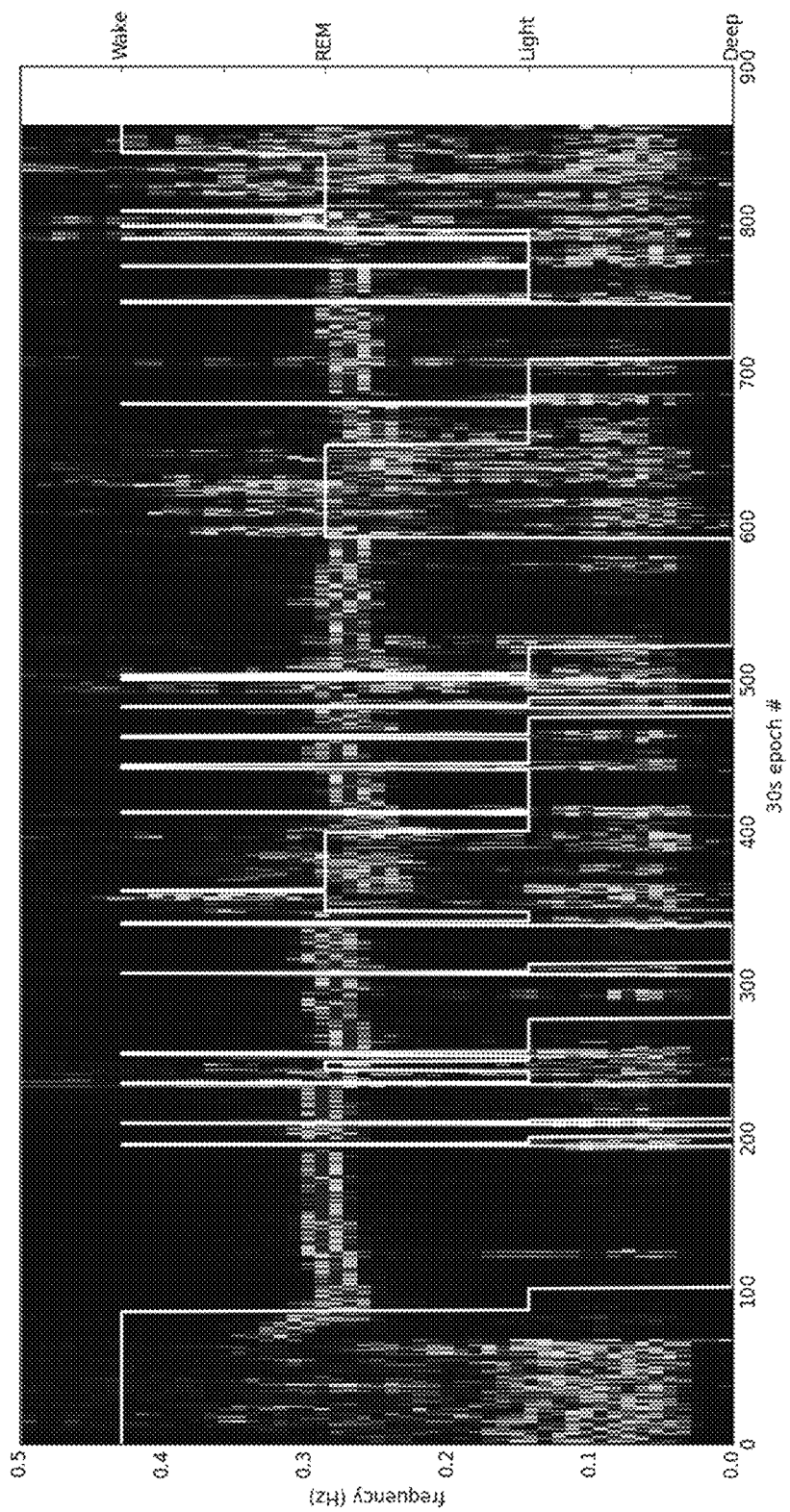
FIG. 1(a) illustrates a classifier according to an aspect of the present invention.

FIG. 1 is a schematic representation of the described systems and methods contained within the data acquisition device 101. In an aspect, the data acquisition device 101, through the use of non-invasive technologies, including, but not limited to, piezo-electric accelerometers for detecting motion, and ECG and PPG recorders, allows for the collection of an abundance of physiological signals during sleep. In an aspect, the data acquisition device 101 is a wearable device. Such wearable devices 101 can include, but are not limited to, the wearable data acquisition device disclosed in U.S. patent application Ser. No. 14/128,675, incorporated in its entirety by reference.

In an aspect, the cardiac and motion signals can be collected within time windows 106. The time windows 106 can come in various lengths. For example, with reference to FIG. 1, a common time window 106 of 3.5 minutes for simultaneously collecting cardiac and motion signals is utilized. In other aspects, other time windows can be used. The cardiac and motion signals can be captured across several time windows 106, forming a series of windows 106, with each window 106 including the same number of samples (i.e., having the same length). In an aspect, to keep track of the windows, the initial window is equal to n. As data collection progresses continuously, windows 106 accumulate as a series of (n+1), (n+2), (n+3), etc., and/or (n−1), (n−2), (n−3), etc. In some cases, window overlap can occur, which can deliver more frequent output. Vectors, (i.e., a matrix which shows input values and can be subjected to transformations) can be produced for both events (i.e. overlapping and non-overlapping windows).

Referring to FIG. 1, the starting point for the windows 106 is the point where raw cardio and motion signals may be either detected by a data acquisition device 101, and/or are communicated from any point of origin so as to be suitable for processing. Through the data acquisition device 101, channels 102 such as ECG 102(*a*) and PPG 102(*b*) enable the extraction of accurate estimates as to when each heartbeat of the subject is initiated. After digital signal processing (DSP) 103, the distance between the onset of successive heartbeats provides information that resembles the so called RR intervals 104, referring to the time between two R-spikes obtained from an ECG 102(*a*) data stream. The heart activity measured by this signal can be modulated by several physiological factors. These factors, for example, the sympathetic nervous system tone that affects heart rate, manifest to different degrees and are predominantly dependent on the sleep/wake state of the wearer. Other factors include, but are not limited to, wake/sleep state, sleep stage, breathing rate and through breathing rate effects by diseases that affect respiration such as COPD.

In addition to heart activity, motion data can be collected from the subject by the data acquisition device 101, simultaneously to cardio data and within the common time window 106 (e.g. 3.5 minutes). In an aspect, the data acquisition device 101 can utilize an accelerometer 102(*c*) and/or a BCG recorder 102(*d*) to acquire the motion data. The resulting data stream reflecting motion is affected by an ample range of physiological states 108, including, but not limited to, restless legs syndrome, sleep epilepsy, obstructive sleep apnea, and other sleep related breathing disorders, as well as sleep/wake stages where rapid eye movement (REM) sleep occurs, during which the voluntary muscles are paralyzed and barely contribute to the signal. For insomnia and related conditions, the motion data stream can also carry information on the quality and stability of sleep.

Inferences on many of the mentioned states above can be made by analyzing how signals in the heart activity channel 102s (a-b) relate to those recorded in the motion channels 102(*c-d*). In an aspect, a set of features including, but not limited to, the cross-spectral density (CSD) 105 of both the cardio and motion channels 102(*a-d*) is computed in order to quantify the common underlying states that generate both the aforementioned cardio and motion data. The CSD 105 finds the period wherein two signals most strongly correlate with each other. In an aspect, for heart rate and breathing rate data, this will happen at the length of one breath (around 5 seconds), since breathing modulates heart rate. The resultant relation between said channels 102(*a-d*) is itemized in terms of the individual constituent frequencies, and how strongly each is affected by common underlying states. In an aspect, the CSD 105 can be determined by CSD software 207, discussed below. This analysis provides information on communal processes to find shared evidence in both motion and cardiac activity data, and itemizes the shared information in terms of the individual constituent frequencies and how strongly each is affected by common underlying states. The aforementioned states that can be inferred using this approach and, for example, be used to aid home based sleep analysis and automated screening of patients with sleep disorders.

The complex relationship between a cross-spectral density vector and a specific physiological state is addressed through the use of a machine learning/statistical approach on real subject data, to train a classifier 107 that can distinguish between all the different states mentioned. For example, the CSD 105 is calculated to determine the dominant frequency (or period) at which the heart rate and breathing rate signals couple, with the heart rate measured via PPG and breathing rate measured via accelerometer channel. The frequency becomes one of many features (e.g., heart rate itself, heart rate variability) that are supplied into a machine learning training algorithm. Further, sleep polysomnography data is supplied, which tells the machine learning training algorithm what sleep/wake stages are associated with the set of features that has been passed to it. In an aspect, the sleep polysomnography data is general data, and not specific to the subject being monitored. However, in other aspects, the sleep polysomnography can be from the subject collected at a previous time. In an aspect, this information can be exemplified in a thirty second epochs because polysomnography sleep scorers monitor sleep in windows of that length (in this case the windows are non-overlapping).

Similarly, many other metrics, such as the spectral coherence, can also be calculated as input to the aforementioned machine learning layer, to map shared activity between the channels to physiological states. Spectral coherence is used to determine the frequencies at which two signals most strongly influence each other. It is closely related to cross-spectral density described above mathematically, but includes extra terms for normalizing the native activity in each channel. As the degree of influence of breathing rate on heart rate changes between different sleep states, this value of spectral coherence also changes. This degree of influence of breathing rate on heart rate (respiratory sinus arrhythmia) strongly depends on sympathetic/parasympathetic balance—when parasympathetic activity dominates, breathing rate most strongly influences heart rate. States of stress or exercise increase sympathetic tone and hence lowers the influence of breathing rate on heart rate.

In an aspect, the system can be configured to calculate a quality metric that allows for conditional prediction of the underlying biological states. The quality metric can be used to indicate the quality of the signal received. For example, the quality metric can include taking a Fourier spectrum of the signal at the ratio of power in the frequency band of the signal that is being tracked to the power in the remainder of the spectrum. In the best case scenario all power is due to the signal, but in the reality noise can make up nearly as much of the total activity in the signal. Therefore, the quality metric can be established to indicate the quality of the signal (i.e., actual activity v. noise). In addition, the quality metric can be configured to limit predictions to periods when data of a sufficient quality is collected. For example, when a subject is sleeping, and the device 101 measure the breathing rate of the subject, there are times when a subject would sleep on a wrist and no breathing signal is available for performing the calculation. In such instances, the system will not make use of HR-BR coupling features in the machine learning algorithm to score sleep, but the remaining features instead.

As discussed above, the system can be configured to determine sleep disorders. For example, the system can detect the presence of narcolepsy in a subject through distinguishing between the REM and wake states by identifying the early/direct transition from wakefulness to REM during a sleep session. Other sleep disorders can be determined as well.

In an aspect, the system can include multiple data acquisition device(s) 101 operating to collect the data. As discussed above, the data collected by data acquisition device(s) can also be sent to and relayed between other data acquisition device(s), a mobile device and/or a cloud based platform, through wireless connections and communications. From either the data acquisition device, the mobile device, and/or the cloud based platform, information can be shared with third parties exemplified by, but not limited to medical care, insurance and healthcare providers.

Figure 2:
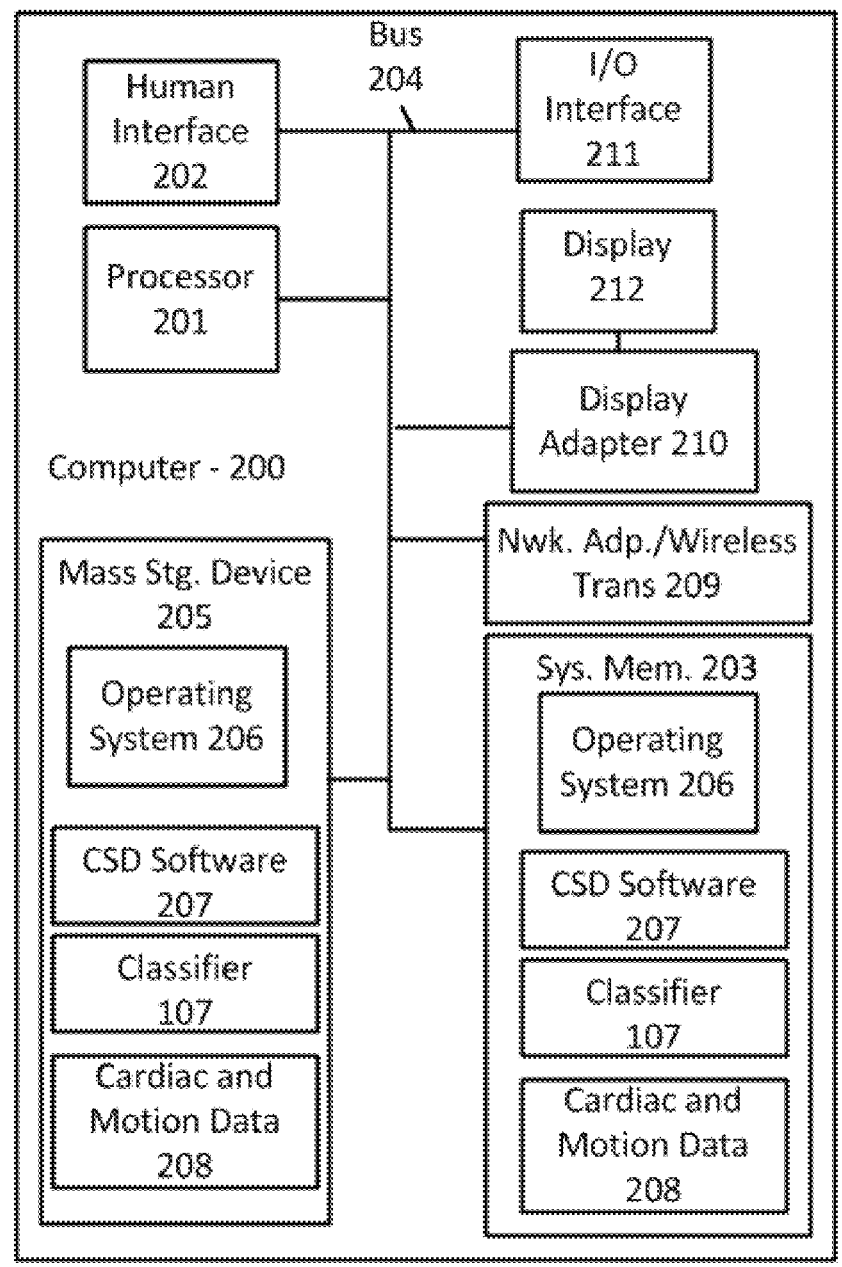
FIG. 2 illustrates a block diagram of a computer according to an aspect of the present invention.

As discussed above, the systems and methods utilize computers and software in order to determine the relationships between the different data signals. FIG. 2 is a block diagram illustrating a computer 200 that is an exemplary operating environment for performing a portion of disclosed methods according to an embodiment of the present invention. This exemplary operating environment is only an example of an operating environment and is not intended to suggest any limitation as to the scope of use or functionality of operating environment architecture. Neither should the operating environment be interpreted as having any dependency or requirement relating to any one or combination of components illustrated in the exemplary operating environment.

Further, one skilled in the art will appreciate that the systems and methods disclosed herein can utilize a general-purpose computing device in the form of a computer 200. For example, the computer 200 performs the duties and responsibilities of computing the CSD 105 of both the cardio and motion channels, wirelessly communicating with other devices, and various other discussed processes. In addition, the computer 200 can be contained with the data acquisition device 101 itself, be a part of a cloud-based platform (with the collected data from the data acquisition device 101 being transmitted), or some other device.

The components of the computer 200 can comprise, but are not limited to, one or more processors or processing units 201, a human interface 202, system memory 203, and a system bus 204 that couples various system components including the processor 201 to the system memory 202. In the case of multiple processing units 201, the computer 200 can utilize parallel computing.

The system bus 204 represents one or more of several possible types of bus structures, including a memory bus or memory controller, a peripheral bus, an accelerated graphics port, and a processor or local bus using any of a variety of bus architectures. By way of example, such architectures can comprise an Industry Standard Architecture (ISA) bus, a Micro Channel Architecture (MCA) bus, an Enhanced ISA (EISA) bus, a Video Electronics Standards Association (VESA) local bus, an Accelerated Graphics Port (AGP) bus, and a Peripheral Component Interconnects (PCI), a PCI-Express bus, a Personal Computer Memory Card Industry Association (PCMCIA), Universal Serial Bus (USB) and the like. The bus 204, and all buses specified in this description can also be implemented over a wired or wireless network connection and each of the subsystems, including the processor 201, a mass storage device 205, an operating system 206, CSD software 207, the classifier 107, cardiac and motion data 208, a network adapter/wireless transceiver 209, an Input/Output Interface 211, a display adapter 210, and a display device 212.

The computer 200 typically comprises a variety of computer readable media. Exemplary readable media can be any available media that is accessible by the computer 200 and comprises, for example and not meant to be limiting, both volatile and non-volatile media, removable and non-removable media. The system memory 203 comprises computer readable media in the form of volatile memory, such as random access memory (RAM), and/or non-volatile memory, such as read only memory (ROM). The system memory 203 typically contains data such as cardiac and motion data 208 and/or program modules such as operating system 206, the classifier 107, and CSD software 207 that are immediately accessible to and/or are presently operated on by the processing unit 201.

In another aspect, the computer 200 can also comprise other removable/non-removable, volatile/non-volatile computer storage media. By way of example, FIG. 2 illustrates a mass storage device 205, which can provide non-volatile storage of computer code, computer readable instructions, data structures, program modules, and other data for the computer 200. For example and not meant to be limiting, a mass storage device 205 can be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

Optionally, any number of program modules can be stored on the mass storage device 205, including by way of example, an operating system 206 and CSD software 207. Cardiac and motion data 208 can also be stored on the mass storage device 205. Cardiac and motion data 208 can be stored in any of one or more databases known in the art. Examples of such databases include DB2®, Microsoft® Access, Microsoft® SQL Server, Oracle®, mySQL, PostgreSQL, and the like. The databases can be centralized or distributed across multiple systems.

In another aspect, the user can enter commands and information into the computer 200 via an input device (not shown). Examples of such input devices comprise, but are not limited to, a keyboard, pointing device (e.g., a "mouse"), a touchscreen interface, a microphone, a joystick, a scanner, tactile input devices such as gloves, and other body coverings, and the like. These and other input devices can be connected to the processing unit 201 via a human machine interface 202 that is coupled to the system bus 204, but can be connected by other interface and bus structures, such as a parallel port, game port, an IEEE 1394 Port (also known as a Firewire port), a serial port, or a universal serial bus (USB).

In yet another aspect, a display device 212 can also be connected to the system bus 204 via an interface, such as a display adapter 210. It is contemplated that the computer 200 can have more than one display adapter 210 and display device 212. For example, a display device can be a monitor, an LCD (Liquid Crystal Display), or a projector. In addition to the display device 212, other output peripheral devices via the Input/Output Interface 211. Any step and/or result of the methods can be output in any form to an output device. Such output can be any form of visual representation, including, but not limited to, textual, graphical, animation, audio, tactile, and the like.

Having thus described exemplary embodiments of a method to determine sleep stages and other related data, it should be noted by those skilled in the art that the within disclosures are exemplary only and that various other alternatives, adaptations, and modifications may be made within the scope of this disclosure. Accordingly, the invention is not limited to the specific embodiments as illustrated herein, but is only limited by the following claims.

What is claimed is:

1. A method to assess sleep physiological states of a subject, comprising:
    a) selecting from a plurality of inputs, at least two measured signals containing degrees of cardiac activity and motion data of the subject;
    b) performing a cross-spectral density calculation on said at least two measured signals to determine the degree of shared activity over a range of frequencies in said at least two measured signals;
    c) calculating a quality metric based on the quality of each of the at least two measured signals, wherein the quality metric is based on each signal itself;
    d) using the shared activity features to classify different underlying physiological states of the subject, wherein the quality metric allows for conditional prediction of the different underlying physiological states to limit predictions to periods when signals of sufficient quality are measured; and
    e) displaying or transmitting the classified underlying physiological states of the subject.

2. The method of claim 1, further comprising using spectral coherence with the performing the cross-spectral density calculation to detect shared activity at different frequencies between the cardiac activity and the motion data.

3. The method of claim 1, wherein the physiological states comprise sleep stages, sleep pathologies, and sleep quality.

4. The method of claim 1, wherein the method is configured to detect narcolepsy, the method further comprising distinguishing between rapid eye movement (REM) sleep and wake states, wherein narcolepsy is detected by means of identifying the early or direct transition from wakefulness to REM sleep during a sleep session.

5. The method of claim 1, wherein the at least two measured signals are collected by a data acquisition device, wherein the data acquisition device is configured to wirelessly communicate data to other devices or platforms.

6. The method of claim 5, wherein the data from said data acquisition device is wirelessly communicated to a cloud-based platform.

7. The method of claim 1, further comprising utilizing contextual data to classify different underlying physiological states of the subject.

8. The method of claim 1, wherein the cardiac activity is captured by an electrocardiogram (ECG) recorder or a photoplethysmograph (PPG) recorder.

9. The method of claim 1, wherein the motion data is captured by an accelerometer or a ballistocardiograph (BCG) recorder.

10. The method of claim 1, wherein the plurality of inputs are collected in time windows.

11. The method of claim 1, wherein using the shared activity features to classify different underlying physiological states further comprises using polysomnography data.

12. The method of claim 1, wherein the quality metric is determined by creating a signal to noise ratio.

13. A system for non-invasive assessment of sleep physiological states of a subject comprising:
    a. a data acquisition device, the data acquisition device configured to select from a plurality of inputs at least two measured signals containing degrees of cardiac activity and motion data of the subject; and
    b. a computing device, the computing device configured to:
        i. perform a cross-spectral density calculation on said at least two measured signals to determine the degree of shared activity over a range of frequencies in the at least two measured signals;
        ii. calculate a quality metric of each of the at least two measured signals, wherein the quality metric is based on each signal itself;
        iii. use the shared activity features to classify different underlying physiological states of the subject, wherein the quality metric allows for conditional prediction of the different underlying physiological states to limit predictions to periods when data of sufficient quality is collected; and
        iv. display or transmit the classified underlying physiological states of the subject.

14. The system of claim 13, wherein the data acquisition device comprises a wearable device.

15. The system of claim 13, wherein the computing device is further configured to use spectral coherence with the cross-spectral density calculation to detect shared activity at different frequencies between the cardiac channel and the motion channel.

16. The system of claim 13, wherein the data acquisition device further comprises an electrocardiogram (ECG) recorder, a photoplethysmograph (PPG) recorder, an accelerometer, and a ballistocardiograph (BCG) recorder, wherein the ECG recorder and the PPG recorder are configured to produce the signals of the cardiac data and the accelerometer and the BCG recorder are configured to produce the signals of the motion data.

17. The system of claim 13, wherein the computing device is configured to obtain contextual data from the subject, wherein the contextual data is used in the classifying of the different underlying physiological states of the subject.

18. The method of claim 1, wherein the at least two measured signals further comprises at least four measured signals.

19. The method of claim 18, wherein the at least four measured signals include at least two cardiac activity signals and at least two motion data signals.

20. The system of claim 13, wherein the quality metric is determined by creating a signal to noise ratio.

* * * * *